(12) United States Patent
Chen et al.

(10) Patent No.: US 11,370,722 B2
(45) Date of Patent: Jun. 28, 2022

(54) METHOD FOR PRODUCING LONG-CHAIN ALKYLBENZENE

(71) Applicant: Nanjing Chemistry New Energy Technology Co. Ltd., Nanjing (CN)

(72) Inventors: Xiwu Chen, Nanjing (CN); Jian Chen, Nanjing (CN); Weituo Xie, Nanjing (CN); Xunda Dai, Nanjing (CN)

(73) Assignee: Nanjing Chemistry New Energy Technology Co. Ltd., Nanjing (CN)

( * ) Notice: Subject to any disclaimer, the term of this patent is extended or adjusted under 35 U.S.C. 154(b) by 0 days.

(21) Appl. No.: 17/157,112

(22) Filed: Jan. 25, 2021

(65) Prior Publication Data
US 2021/0395166 A1   Dec. 23, 2021

(30) Foreign Application Priority Data
Jun. 22, 2020 (CN) .......................... 202010572577.5

(51) Int. Cl.
*C07C 2/12* (2006.01)
*C07C 15/42* (2006.01)
(Continued)

(52) U.S. Cl.
CPC ................. *C07C 2/12* (2013.01); *B01J 38/12* (2013.01); *B01J 38/20* (2013.01); *C07C 15/42* (2013.01)

(58) Field of Classification Search
CPC .... C07C 2/00; C07C 2/02; C07C 2/08; C07C 2/12; C07C 2/54; C07C 2/64; C07C 2/66; C07C 15/42; C07C 2/70; C07C 2529/70; C07C 2529/78; B01J 38/12; B01J 38/02; B01J 38/14; B01J 38/20; B01J 29/041;
(Continued)

(56) References Cited

U.S. PATENT DOCUMENTS

| | | | |
|---|---|---|---|
| 4,954,325 | A | 9/1990 | Rubin et al. |
| 5,034,564 | A | 7/1991 | Kocal |

(Continued)

FOREIGN PATENT DOCUMENTS

| | | |
|---|---|---|
| CN | 1332140 A | 1/2002 |
| CN | 1107645 C | 5/2003 |

(Continued)

*Primary Examiner* — In Suk C Bullock
*Assistant Examiner* — Jason Y Chong
(74) *Attorney, Agent, or Firm* — The Ollila Law Group LLC (57) ABSTRACT

The present invention relates to a method for producing long-chain alkylbenzene by reacting an aromatic hydrocarbon and a long-chain olefin, wherein the reaction is carried out in the presence of a solid acid catalyst, the aromatic hydrocarbon is selected from the group consisting of benzene, toluene and xylene, the long-chain olefin is selected from the group consisting of $C_8$-$C_{26}$ alkenes, the catalyst is a HMCM-22 type molecular sieve solid acid catalyst modified with heteroatom(s), the heteroatom(s) is/are selected from the group consisting of boron, gallium, indium, chromium, molybdenum, tungsten, manganese and phosphorus, and the molar ratio of silicon atoms to heteroatoms in the solid acid catalyst is in the range of 1:0.01-0.03. The invention also relates to a method for regenerating the solid acid catalyst used in the reaction.

14 Claims, 2 Drawing Sheets

(51) Int. Cl.
*B01J 38/12* (2006.01)
*B01J 38/20* (2006.01)

(58) Field of Classification Search
CPC   B01J 29/7038; B01J 29/7088; B01J 29/7876;
B01J 29/90; B01J 35/002; B01J 35/1019;
B01J 35/1047; B01J 37/28; B01J
2229/186; Y02P 20/584
See application file for complete search history.

(56) References Cited

U.S. PATENT DOCUMENTS

| | | |
|---|---|---|
| 5,196,574 A | 3/1993 | Kocal |
| 5,344,997 A | 9/1994 | Kocal |
| 5,648,579 A | 7/1997 | Kulprathipanja et al. |
| 7,199,068 B2 | 4/2007 | Winder et al. |
| 2003/0028060 A1* | 2/2003 | Dandekar ................ C07C 2/66 |
| | | 585/467 |

FOREIGN PATENT DOCUMENTS

| | | |
|---|---|---|
| CN | 1514816 A | 7/2004 |
| CN | 1638870 A | 7/2005 |
| CN | 1868984 A | 11/2006 |
| CN | 101058523 A | 10/2007 |
| CN | 101130477 A | 2/2008 |
| CN | 102464539 A | 5/2012 |
| CN | 103130596 A | 6/2013 |
| WO | 9823560 A1 | 6/1998 |
| WO | 02100807 A1 | 12/2002 |

* cited by examiner

METHOD FOR PRODUCING LONG-CHAIN ALKYLBENZENE

TECHNICAL FIELD

The present invention relates to a method for producing long-chain alkylbenzene. In particular, the present invention relates to a method for producing long-chain alkylbenzene by using a solid acid catalyst, and to a method for regenerating the solid acid catalyst used therein.

BACKGROUNDS

Long-chain alkylbenzenes are important organic chemical raw materials in the field of petrochemical industry. $C_{10}$-$C_{13}$ linear alkylbenzenes (which means linear alkylbenzene with $C_{10}$-$C_{13}$ alkyl) are main raw materials for the production of surfactant for detergents. $C_{20}$-$C_{24}$ linear alkylbenzenes (which means linear alkylbenzene with $C_{20}$-$C_{24}$ alkyl) are sulfonated to provide $C_{20}$-$C_{24}$ alkylbenzene sulfonic acids, and calcium alkylbenzene sulfonate with higher carbon numbers is obtained after a neutralization process. Calcium alkylbenzene sulfonate with higher carbon numbers is one of lubricating oil additives, and is mainly used to produce detergent and dispersant. $C_{12}$ linear olefin, made from tetramerization of propylene or trimerization of butene, is used for alkylation of benzene to produce $C_{12}$ alkylbenzene (which means linear alkylbenzene with $C_{12}$ alkyl), which is mainly used to produce calcium salt of sulfonic acid for pesticide emulsifiers. Alkylbenzenes produced by alkylation of benzene, toluene or xylene with $C_{16}$-$C_{18}$ olefins are main raw materials for the production of oil-displacing agents for oil recovery.

In the past, the preparation of many alkylbenzene products involves the using of corrosive liquid acids such as $H_2SO_4$, HF, $AlCl_3$, and the like. However, such liquid acids have problems such as corrosion of equipments, environmental pollution, difficult separation of catalysts, poor product quality, and the like. Compared with liquid acid catalysts, solid acid catalysts have higher activity and selectivity for a number of chemical reactions, are non-toxic, non-corrosive to equipment, regenerable and recyclable, environmentally friendly, and have broad prospects in industrial application.

In U.S. Pat. Nos. 5,034,564, 5,196,574, 5,344,997, 5,648,579, and CN1332140A, UOP Corporation of the United States discloses a process for producing alkylbenzene for detergents by using the alkylation reaction of benzene and long-chain olefins under the action of a solid acid catalyst. The catalyst used in the invention is a solid acid catalyst of the type of fluorine-containing aluminosilicates. The weight ratio of silicon to aluminum of the catalyst is 65:35-85:15, and the weight percentage of fluorine is 1.5%-3.5%. The reaction temperature is 100-225° C., the reaction pressure is 2-3.5 MPa, the liquid hourly space velocity of the olefin feed is 0.3-6 $hr^{-1}$, and the molar ratio of benzene to olefin is 30-1. The olefin conversion is greater than 98%, the monoalkylbenzene selectivity is greater than 85%, and the linear chain rate is greater than 90%. The duration of alkylation reaction is about 10-48 hours, and then the catalyst is regenerated by washing with hot benzene. The regeneration temperature is 150-350° C., the regeneration pressure is 2-5 MPa, the liquid hourly space velocity of the regeneration benzene is 0.1-1 $hr^{-1}$, and the regeneration duration is 10-30 hours.

Patents CN1868984A, CN101058523A, and CN102464539A report solid acid catalysts prepared by modifying molecular sieves HMCM-41, SBA-15, HY, USY, HZSM-20, M-KIT and the like, and CN103130596A reports a preparation method of solid super acid Ni/$SO_4^{-2}$—$SnO_2$ catalyst. Such solid acids are used in the reaction of $C_{10}$-$C_{13}$ long-chain olefin and benzene to produce detergent alkylbenzene.

Patent CN101130477A reports that the preparation of a new solid acid catalyst by immobilizing $AlCl_3$ onto $Al_2O_3$, $SiO_2$, $Al_2O_3$—$SiO_2$ or silica-alumina molecular sieve carriers, which catalyst is used to prepare branched long-chain alkylbenzenes from alkylation reaction of short-chain alkylbenzene, particularly toluene and xylene, and long-chain olefin, wherein the branched long-chain alkylbenzenes are mainly used in the preparation of surfactants for tertiary oil recovery.

In 1990, Mobil Corporation of the United States first reported the synthesis of MCM-22 type molecular sieve in U.S. Pat. No. 4,954,325. The MCM-22 type molecular sieve has broad application prospects in catalytic cracking, isomerization, methane non-oxidative aromatization, alkylation and the like, because the MCM-22 type molecular sieve comprises two pore systems of 10-membered ring and 12-membered ring, and as a catalyst carrier, it has good hydrothermal stability, large pore structure, large specific surface area and micropore volume.

Patent CN1107645C reports a synthesis method of MCM-22 type molecular sieve. The method includes formulating silicon source, aluminum source, base source, organic template agent and water in a certain proportion so as to form a synthetic colloid and subjecting the synthetic colloid to a hydrothermal crystallization. It is characterized by hydrothermal crystallization at 160-200° C. for 1-20 hours, and then reducing the temperature to 130-155° C. and crystallizing for additional 8-100 hours.

Patent CN1638870A reports a method for regenerating a solid acid catalyst, wherein the method is carried out as follows: when the activity of the solid acid catalyst decreases, the solid acid catalyst is washed by a mixture of an aromatic hydrocarbon, which is one of the reactants, and a suitable alkane to dissolve the colloid substances deposited on the catalyst, so as to achieve the regeneration of the catalyst.

Patents WO98/23560 and CN1514816A disclose a method for regenerating a solid acid alkylation catalyst. The method includes the regenerating of deactivated catalyst by using the formed alkylate as a washing agent in the presence of hydrogen.

Unlike the synthesis of ethylbenzene from a short-chain olefin such as ethylene and benzene, long-chain olefins tend to carbonization and coking on solid acid catalyst during the production of long-chain alkylbenzenes. In the alkylation process of a long chain olefin and an aromatic hydrocarbon, 2-position alkylbenzene product is particularly desirable. In the process of producing long-chain alkylbenzenes by using a solid acid catalyst, there are many problems such as rapid deactivation due to the insufficient stability of solid acid catalysts, difficult regeneration, insufficient yield and selectivity of target alkylbenzene products, and the like. Therefore, a method for producing long-chain alkylbenzenes which can avoid at least some of above defects is desirable.

SUMMARY OF THE INVENTION

An object of the present invention is to provide a method for producing long-chain alkyl benzene which is intrinsically safe, green and environmentally friendly, and to provide a method for regenerating the catalyst used therein. By using the producing method, long-chain alkylbenzenes can be stably produced with high yield and selectivity; and the used catalyst can be regenerated easily by a specific regeneration method, and the performance of the regenerated catalyst is even substantially equivalent to that of fresh catalyst.

It is surprisingly found that above object of the present invention can be achieved by the following technical solutions. According to certain aspects of the present invention, it is provided a method for producing long-chain alkylbenzene by reacting an aromatic hydrocarbon and a long-chain olefin, wherein the reaction is carried out in the presence of a solid acid catalyst, the aromatic hydrocarbon is selected from the group consisting of benzene, toluene and xylene, the long-chain olefin is selected from the group consisting of $C_8$-$C_{26}$ alkenes, the catalyst is a HMCM-22 type molecular sieve solid acid catalyst modified with heteroatom(s), the heteroatom(s) is/are selected from the group consisting of boron, gallium, indium, chromium, molybdenum, tungsten, manganese and phosphorus, and the molar ratio of silicon atoms to heteroatoms in the solid acid catalyst is in the range of 1:0.01-0.03.

It has been found that the solid acid catalyst used according to the present invention is particularly suitable for the preparation of long-chain alkylbenzenes. The solid acid catalyst has high specific surface area and pore volume and has a high total acid amount. In the preparation process of long-chain alkylbenzene, the solid acid catalyst used according to the present invention exhibits high olefin conversion and alkylbenzene selectivity, excellent target alkylbenzene isomer selectivity and high stability, particularly a long continuous running time.

According to certain aspects of the present invention, a method for regenerating a solid acid catalyst is provided, wherein the catalyst is in-situ coke-burning regenerated by using a regeneration gas comprising 1-20 wt %, preferably 2-15 wt % of oxygen and 80-99 wt %, preferably 85-98 wt % of nitrogen, wherein the volumetric space velocity of the regeneration gas is 100-1000 $hr^{-1}$, preferably 300-500 $hr^{-1}$.

It has been found that the solid acid catalyst used according to the present invention can be easily regenerated using the regeneration method mentioned above. The solid acid catalyst regenerated by the regeneration method according to the present invention is also suitable for the preparation of long-chain alkylbenzene. The regenerated solid acid catalyst has high specific surface area, pore volume and total acid amount which are similar to those of fresh solid acid catalyst. In the preparation process of long-chain alkylbenzene, the regenerated solid acid catalyst exhibits high olefin conversion and alkylbenzene selectivity, excellent target alkylbenzene isomer selectivity and high stability, particularly a long continuous running time.

DETAILED DESCRIPTION

Any method steps, processes, and operations described herein are not to be construed as necessarily requiring their performance in the particular order discussed or illustrated, unless obvious different meaning appears according to the context. It is also to be understood that additional or alternative steps may be employed, unless otherwise indicated.

Herein, disclosure of ranges includes disclosure of all values and further divided ranges within the entire range, including endpoints and sub-ranges given for the ranges.

Herein, when referring to the concentration of a substance or the concentration of a substance in a solution, it refers to the concentration in percentage by weight, unless otherwise specified.

According to the first embodiment of the present invention, there is provided a method for producing long-chain alkylbenzene by reacting an aromatic hydrocarbon and a long-chain olefin, characterized in that the reaction is carried out in the presence of a solid acid catalyst, the aromatic hydrocarbon is selected from the group consisting of benzene, toluene and xylene, the long-chain olefin is selected from the group consisting of $C_8$-$C_{26}$ alkenes, the catalyst is preferably a HMCM-22 type molecular sieve solid acid catalyst modified with heteroatom(s) during crystallization process, the heteroatom(s) is/are selected from the group consisting of boron, gallium, indium, chromium, molybdenum, tungsten, manganese and phosphorus, and the molar ratio of silicon atoms to heteroatoms in the solid acid catalyst is in the range of 1:0.01-0.03.

According to the second embodiment of the present invention, the method according to the first embodiment is provided, characterized in that the reaction uses a fixed bed reactor so as to carry out a continuous liquid phase reaction, wherein the reaction temperature is from 100 to 300° C., the reaction pressure is from 1 to 5 MPa, and the liquid hourly space velocity of the reaction in terms of olefin is from 0.1 to 5 $Hr^{-1}$.

According to the third embodiment of the present invention, a method according to the first embodiment or the second embodiment is provided, characterized in that the molar ratio of aromatic hydrocarbon to long-chain olefin is from 1 to 30.

According to the fourth embodiment of the present invention, a method according to one of the preceding embodiments is provided, characterized in that the catalyst is prepared by a method comprising the following steps:
a) formulating silicon source, aluminum source, heteroatom modifier, pH regulator, organic template agent and water in a certain proportion so as to form a synthetic colloid, and subjecting the synthetic colloid to a hydrothermal crystallization;

b) filtering, washing and drying the crystallized product and calcining at 500-600° C. to remove the template agent so as to obtain Na or K form MCM-22 type molecular sieve;

c) exchanging the molecular sieve into HMCM-22 type molecular sieve by using ammonium chloride and/or ammonium nitrate as exchanger, wherein the Na or K content of the HMCM-22 type molecular sieve after exchanging is less than 1000 ppm, and drying and roasting the HMCM-22 type molecular sieve so as to obtain a heteroatom-modified HMCM-22 type molecular sieve;

d) adding a binder into the HMCM-22 type molecular sieve, shaping, drying, and calcining at 500-600° C. so as to obtain the HMCM-22 type molecular sieve solid acid catalyst.

According to the fifth embodiment of the present invention, a method according to one of the preceding embodiments is provided, characterized in that the silicon source is selected from the group consisting of silica gel, silica sol, water glass, silicic acid, sodium silicate, methyl orthosilicate, and ethyl orthosilicate.

According to the sixth embodiment of the present invention, a method according to one of the preceding embodiments is provided, characterized in that the aluminum source is selected from the group consisting of sodium metaaluminate, aluminum sulfate, aluminum nitrate, and pseudo-boehmite.

According to the seventh embodiment of the present invention, a method according to one of the preceding embodiments is provided, characterized in that the organic template agent is selected from the group consisting of hexamethyleneimine, caprolactam and piperidine.

According to the eighth embodiment of the present invention, a method according to one of the preceding embodiments is provided, characterized in that the pH regulator is selected from the group consisting of potassium hydroxide and sodium hydroxide.

According to the ninth embodiment of the present invention, a method according to one of the preceding embodiments is provided, characterized in that the heteroatom modifier is selected from the group consisting of phosphoric acid, sodium tungstate and gallium nitrate.

According to the tenth embodiment of the present invention, a method according to one of the preceding embodiments is provided, characterized in that the molar ratio of the silicon source, aluminum source, heteroatom modifier, pH regulator, organic template agent and water $SiO_2:Al_2O_3:OH^-:M:TA:H_2O=1:0.01-0.1:0.1-0.5:0.01-0.03:0.3-0.6:20-50$, preferably $SiO_2:Al_2O_3:OH^-:M:TA:H_2O=1:0.05-0.08:0.2-0.3:0.01-0.02:0.4-0.5:30-40$, where $SiO_2$ represents the silicon source calculated by $SiO_2$, $Al_2O_3$ represents the aluminum source calculated by $Al_2O_3$, $OH^-$ represents the pH regulator calculated by $OH^-$, TA represents the organic template agent, and M represents the heteroatoms in the heteroatom modifier.

According to the eleventh embodiment of the present invention, a method according to one of the preceding embodiments is provided, characterized in that, after the activity of the catalyst decreases, the catalyst is in-situ coke-burning regenerated by using an oxygen-containing inert gas, and during the coke-burning regeneration process, the temperature ramp rate for coke-burning is controlled by arranging five temperature stages.

According to the twelfth embodiment of the present invention, a method according to one of the preceding embodiments is provided, characterized in that the catalyst is in-situ coke-burning regenerated by using a regeneration gas comprising 1-20 wt %, preferably 2-15 wt % of oxygen and 80-99 wt %, preferably 85-98 wt % of nitrogen, and the volumetric space velocity of the regeneration gas is 100-1000 $hr^{-1}$, preferably 300-500 $hr^{-1}$.

According to the thirteenth embodiment of the present invention, a method according to one of the preceding embodiments is provided, characterized in that five coke-burning temperature stages are arranged, i.e. room temperature, 200° C., 350° C., 450° C. and 520° C., wherein the temperature ramp rate from room temperature to 200° C. is controlled at 10-40° C./h, preferably 20-30° C./h, and the temperature is maintained at 200° C. for 5-12 h, preferably 6-10 h; the temperature ramp rate from 200° C. to 350° C. is controlled at 15-25° C./h, preferably 18-22° C./h, and the temperature is maintained at 350° C. for 5-12 h, preferably 6-10 h; the temperature ramp rate from 350° C. to 450° C. is controlled at 10-30° C./h, preferably 15-25° C./h, and the temperature is maintained at 450° C. for 5-12 h, preferably 6-10 h; and the temperature ramp rate from 450° C. to 520° C. is controlled at 5-15° C./h, preferably 8-12° C./h, and the temperature is maintained at 520° C. for 5-10 h, preferably 6-8 h.

According to the fourteenth embodiment of the present invention, a method for regenerating a solid acid catalyst is provided, wherein the catalyst is in-situ coke-burning regenerated by using a regeneration gas comprising 1-20 wt %, preferably 2-15 wt % of oxygen and 80-99 wt %, preferably 85-98 wt % of nitrogen, wherein the volumetric space velocity of the regeneration gas is 100-1000 $hr^{-1}$, preferably 300-500 $hr^{-1}$.

According to the fifteenth embodiment of the present invention, the regeneration method according to the fourteenth embodiment is provided, characterized in that five coke-burning temperature stages are arranged, i.e. room temperature, 200° C., 350° C., 450° C. and 520° C., wherein the temperature ramp rate from room temperature to 200° C. is controlled at 10-40° C./h, preferably 20-30° C./h, and the temperature is maintained at 200° C. for 5-12 h, preferably 6-10 h; the temperature ramp rate from 200° C. to 350° C. is controlled at 15-25° C./h, preferably 18-22° C./h, and the temperature is maintained at 350° C. for 5-12 h, preferably 6-10 h; the temperature ramp rate from 350° C. to 450° C. is controlled at 10-30° C./h, preferably 15-25° C./h, and the temperature is maintained at 450° C. for 5-12 h, preferably 6-10 h; and the temperature ramp rate from 450° C. to 520° C. is controlled at 5-15° C./h, preferably 8-12° C./h, and the temperature is maintained at 520° C. for 5-10 h, preferably 6-8 h.

According to an aspect of the present invention, the catalyst is a solid acid catalyst. According to a preferred aspect of the present invention, the solid acid catalyst is preferably a HMCM-22 type molecular sieve catalyst modified by incorporating a heteroatom during the crystallization process, wherein the heteroatom(s) is/are selected from the group consisting of boron, gallium, indium, chromium, molybdenum, tungsten, manganese and phosphorus. Preferably, the heteroatom(s) is/are selected from the group consisting of boron, gallium and phosphorus. In the HMCM-22 type molecular sieve catalyst, the molar ratio of silicon atoms to heteroatoms is in the range of 1:0.01-0.03, preferably in the range of 1:0.01-0.02. Without wishing to be bound by any specific theories, it is believed that the incorporation of heteroatom, which is already carried out during the crystallization process, leads to improved stability of the resulting molecular sieve catalyst, especially maintaining high catalytic performance for a long time in the preparation reaction for long-chain alkylbenzenes.

Preparation of Solid Acid Catalyst

According to an aspect of the present invention, the solid acid catalyst is prepared by a method comprising the following steps:

a) formulating silicon source, aluminum source, heteroatom modifier, pH regulator, organic template agent and water in a certain proportion so as to form a synthetic colloid, and subjecting the synthetic colloid to a hydrothermal crystallization;

b) filtering, washing and drying the crystallized product and calcining at 500-600° C. to remove the template agent so as to obtain Na or K form MCM-22 type molecular sieve;

c) exchanging the molecular sieve into HMCM-22 type molecular sieve by using ammonium chloride and/or ammonium nitrate as exchanger, wherein the Na or K content of the HMCM-22 type molecular sieve after exchanging is less than 1000 ppm, and drying and roasting the HMCM-22 type molecular sieve so as to obtain a heteroatom-modified HMCM-22 type molecular sieve;

d) adding a binder into the HMCM-22 type molecular sieve, extrusion shaping, drying, and calcining at 500-600° C. so as to obtain the HMCM-22 type molecular sieve solid acid catalyst.

According to an aspect of the present invention, in step a), the silicon source is selected from the group consisting of silica gel, silica sol, water glass, silicic acid, sodium silicate, methyl orthosilicate and ethyl orthosilicate.

According to an aspect of the present invention, in step a), the aluminum source is selected from the group consisting of sodium metaaluminate, aluminum sulfate, aluminum nitrate and pseudo-boehmite.

In present invention, the pH regulator refers to a substance used to adjust the pH, which is also referred to as base source. According to an aspect of the present invention, in step a), the pH regulator is selected from the group consisting of potassium hydroxide and sodium hydroxide.

According to an aspect of the present invention, the heteroatom in the heteroatom modifier is selected from the group consisting of boron, gallium, indium, chromium, molybdenum, tungsten, manganese and phosphorus. According to an aspect of the present invention, in step a), examples of the heteroatom modifiers can include boric acid, sodium borate, potassium borate, lithium borate, gallium nitrate, gallium chloride, sodium gallate, potassium gallate, indium nitrate, indium carbonate, indium sulfate, indium trioxide, potassium indiumate, sodium chromate, potassium chromate, sodium dichromate, potassium dichromate, potassium molybdate, sodium molybdate, ammonium molybdate, potassium tungstate, sodium tungstate, ammonium tungstate, potassium manganate, sodium manganate, potassium permanganate, sodium permanganate, phosphoric acid, sodium phosphate, potassium phosphate, ammonium phosphate, metaphosphoric acid, sodium metaphosphate, potassium metaphosphate, and ammonium metaphosphate. Preferably, the heteroatom modifier is selected from the group consisting of phosphoric acid, sodium tungstate and gallium nitrate.

According to an aspect of the present invention, in step a), an organic amine is used as the organic template agent. As examples of organic amine, hexamethylenediamine, ethylenediamine, n-butylamine, pyrrolidine, hexamethyleneimine, caprolactam and piperidine can be mentioned. According to a preferred aspect of the present invention, in step a), the organic template agent is selected from the group consisting of hexamethyleneimine, caprolactam and piperidine. In present invention, the organic template agent is also referred to as template agent.

According to an aspect of the present invention, in step a), a solvent is used. Preferably, water is used as the solvent.

According to an aspect of the present invention, it is found that a molar ratio of silicon atoms to heteroatoms in the solid acid catalyst in the range of 1:0.01-0.03 is particularly suitable for catalyzing long-chain alkylation reaction. A significant exceeding of the upper limit of the range results in a reduced total acid amount and reduced catalytic performance of the resulting catalyst.

According to an aspect of the present invention, in step a), the molar ratio of the silicon source to the aluminum source $SiO_2:Al_2O_3=1:0.01-0.1$, preferably $SiO_2:Al_2O_3=1:0.05-0.08$, wherein $SiO_2$ represents the silicon source calculated by $SiO_2$, and $Al_2O_3$ represents the aluminum source calculated by $Al_2O_3$.

According to an aspect of the present invention, in step a), the molar ratio of the silicon source to the pH regulator $SiO_2:OH^-=1:0.1-0.5$, preferably $SiO_2:OH^-=1:0.2-0.3$, wherein $SiO_2$ represents the silicon source calculated by $SiO_2$, and $OH^-$ represents the pH regulator calculated by $OH^-$.

According to an aspect of the present invention, in step a), the molar ratio of the silicon source to the organic template agent $SiO_2:TA=1:0.3-0.6$, preferably $SiO_2:TA=1:0.4-0.5$, wherein $SiO_2$ represents the silicon source calculated by $SiO_2$, and TA represents the organic template agent.

According to an aspect of the present invention, in step a), the molar ratio of silicon source to water $SiO_2:H_2O=1:20-50$, preferably $SiO_2:H_2O=1:30-40$, wherein $SiO_2$ represents the silicon source calculated by $SiO_2$, and $H_2O$ represents water.

In present invention, "hydrothermal crystallization" refers to a method of forming crystals under high temperature and high pressure in a closed reactor by using an aqueous solution as reaction medium. According to an aspect of the present invention, the above-mentioned materials silicon source, aluminum source, heteroatom modifier, pH regulator, organic template agent and water are uniformly mixed in the proportions listed above to form a gel. The synthesis temperature of the crystallization reaction is controlled to be 150-200° C., preferably 160-190° C. The crystallization reaction is carried out for 24-120 hours, preferably 48-120 hours. The pressure of the crystallization reaction is a self-generated pressure. The crystallization reaction can be carried out either with dynamic stirring or in static state without stirring.

After filtration and washing, the crystallized product is dried at 100-150° C. for 2-10 hours. The temperature is programmably increased to 500-600° C. to remove the organic template agent.

The molecular sieve obtained by removing the organic template agent is in Na form or K form, and should be exchanged into hydrogen form Ammonium chloride and/or ammonium nitrate are used as exchanger. In general, a solution of the exchanger in a solvent, preferably water, is used. The concentration of the exchanger solution is controlled at 5-30% by weight, preferably 10-25% by weight. During the exchanging, the liquid to solid mass ratio of the exchanger solution to the molecular sieve is 2-10. The exchanging temperature is 60-100° C. The duration for each exchanging is 1-10 hours. It can be exchanged for one or more times. The content of Na or K in the exchanged molecular sieve is less than 1000 ppm by weight. After drying and roasting, a heteroatom-modified HMCM-22 type molecular sieve is obtained.

A binder is added to the heteroatom-modified HMCM-22 type molecular sieve, wherein the binder can be alumina, pseudo-boehmite and the like, and is shaped, preferably extrusion shaped. The shaped catalyst is dried at 150-250° C. for 2-10 hours and calcined at 500-600° C. for 2-10 hours so as to obtain HMCM-22 type solid acid catalyst.

According to an aspect of the present invention, the resulting catalyst has a specific surface area of at least 390 m$^2$/g, preferably at least 400 m$^2$/g. The pore volume of the resulting catalyst is at least 0.350 ml/g, preferably at least 0.360 ml/g, more preferably at least 0.370 ml/g. The Lewis acid amount (L acid amount) of the resulting catalyst is at least 2.2*10$^{20}$ sites/g·cat, preferably at least 2.3*10$^{20}$ sites/g·cat. The Bronsted acid amount (B acid amount) of the resulting catalyst is at least 2.6*10$^{20}$ sites/g·cat, preferably at least 2.7*10$^{20}$ sites/g·cat. The total acid amount of the resulting catalyst (Lewis acid amount+Bronsted acid amount) is at least 5.0*10$^{20}$ sites/g·cat, preferably at least 5.1*10$^{20}$ sites/g·cat, more preferably at least 5.2*10$^{20}$ sites/g·cat.

The catalyst prepared according to the present invention exhibits a high stability. In present invention, stability particularly refers to the ability of a catalyst to maintain its catalytic performance in a catalytic reaction for a long time.

Preparation of Long Chain Alkylbenzene

According to an aspect of the present invention, the long-chain olefin refers to linear or branched olefins having from 8 to 26, preferably from 8 to 22, more preferably from 12 to 22 carbon atoms, which can have one, two or more ethylenic double bonds. Specifically, mention can be made of octene, nonene, decene, undecene, dodecene, tridecene, tetradecene, pentadecene, hexadecene, heptadecene, octadecene, nonadecene, eicosene, heneicosene, docosene, tricosene, tetracosene, pentacosene, hexacosene, isomers thereof and mixtures of two or more of them. The long-chain olefins herein also include industrial mixtures produced by oligomerization of propylene, butene and the like, preferably propylene tetramer or butene trimer.

According to an aspect of the present invention, the aromatic hydrocarbon is benzene, toluene, xylene or a mixture thereof.

According to an aspect of the present invention, the aromatic hydrocarbon and long-chain olefin undergo continuous liquid phase reaction in a fixed bed reactor. The catalyst in the fixed bed reactor is the (heteroatom-modified) HMCM-22 type solid acid catalyst prepared as described above. In the reaction, the aromatic hydrocarbon is present at least in equimolar amount relative to the long-chain olefin, preferably in an excess amount. Preferably, the molar ratio of the aromatic hydrocarbon to the long-chain olefin is 1-30. The long chain olefin and aromatic hydrocarbon can be mixed before entering into the reactor. The temperature of the reaction is 100-300° C., preferably 120-200° C., the reaction pressure is 1-5 MPa, preferably 1.5-4.5 MPa, more preferably 2-4 MPa, and the liquid hourly space velocity of the reaction in terms of olefin is 0.1-5 Hr$^{-1}$.

Coke-Burning Regeneration of Catalyst

The activity of the catalyst will decrease after the reaction proceeds for a period of time, and at this time, the catalyst needs to be regenerated. According to an aspect of the present invention, the catalyst which is deactivated after use is regenerated by burning the coke. According to an aspect of the present invention, the coke-burning regeneration is performed in situ. Before burning the coke, the catalyst bed in the reactor can be first purged with steam, and then purged with an inert gas. In the coke-burning process, a mixture containing 1-20 wt %, preferably 2-15 wt % oxygen and 80-99 wt %, preferably 85-98 wt % nitrogen is used as regeneration gas. The volumetric space velocity of the regeneration gas is 100-1000 hr$^{-1}$, preferably 300-500 hr$^{-1}$.

According to an aspect of the present invention, five coke-burning temperature stages are arranged in the coke-burning process, i.e. room temperature and four temperature stages: 200° C., 350° C., 450° C. and 520° C. The temperature ramp rate from room temperature to 200° C. is controlled at 10-40° C./h, preferably 20-30° C./h, and the temperature is maintained at 200° C. for 5-12 h, preferably 6-10 h; the temperature ramp rate from 200° C. to 350° C. is controlled at 15-25° C./h, preferably 18-22° C./h, and the temperature is maintained at 350° C. for 5-12 h, preferably 6-10 h; the temperature ramp rate from 350° C. to 450° C. is controlled at 10-30° C./h, preferably 15-25° C./h, and the temperature is maintained at 450° C. for 5-12 h, preferably 6-10 h; and the temperature ramp rate from 450° C. to 520° C. is controlled at 5-15° C./h, preferably 8-12° C./h, and the temperature is maintained at 520° C. for 5-10 h, preferably 6-8 h.

After the completion of coke-burning, the catalyst cooled naturally.

Measuring Methods:
Characterization of catalyst:
XRD characterization
XRD characterization is conducted on D/max-rb and D/max-2000 X-ray diffractometers of Rigaku, Japan at room temperature. The measuring parameters are as follows:
Measuring conditions:
X-ray tube:
Target: Cu
Voltage: 40(Kv)
Current: 50 (mA)
Slit:
Divergence slit: 1(deg.)
Scattering slit: 1(deg.)
Receiving slit: 0.15(deg.)
scanning:
Scanning range: 5-40(deg.)
Scanning speed: 5(deg/min).

Acid Amount Characterization

The acid amount is characterized by TPD method, wherein it is stipulated that the amount of pyridine adsorbed by the catalyst at 473K is the total acid amount, the amount of adsorbed 2,6-dimethyl pyridine is the B acid amount, and the L acid amount is obtained by subtracting B acid amount from the total acid amount. The calculation formula is:

$$\text{Acid amount} = 6.02 \times 10^{23} \left[ \sum_{1}^{m} (Ae - Ai)/Ae \times V \times \rho / W / M \right]$$

wherein: Ae—area of adsorption equilibrium peak Ai—the peak area of the i injection
V—injection volume (μL) W—catalyst mass (mg)
ρ—adsorbent density (g/mL) m—number of pulses
M—molecular weight of adsorbent (g/mol)
The temperature programmed desorption conditions are as follows:
Catalyst: 50 mg (40-60 mesh) Carrier gas: Helium, flow rate 42 ml/min, heating rate 15° C./min.

Specific Surface Area and Pore Volume

The specific surface area and pore volume characterization are conducted by using ASAP2000 adsorption instrument of Micromeritics Company, USA through low-temperature liquid nitrogen adsorption method, and is calculated by BET.

Characterization of Reacting Raw Materials and Products

The reaction products and raw materials of alkylation of benzene are characterized by measuring bromine value or bromine index through LC-6 micro-coulometric bromine value instrument, and analyzing components of product by GC9000 gas chromatography, and are calculated by the following formula:

$$X = \frac{B_{i\ raw\ material} - B_{i\ product}}{B_{i\ raw\ material}} \times 100\%$$

$$S_{alkylbenzene} = \frac{\sum y_{i\ alkylbenzene}}{\sum y_{i\ alkylbenzene} + \sum y_{i\ heavy\ alkylbenzene}} \times 100\%$$

$$S_{2-alkylbenzene} = \frac{\sum y_{i\ 2-alkylbenzene}}{\sum y_{i\ alkylbenzene} + \sum y_{i\ heavy\ alkylbenzene}} \times 100\%$$

wherein: X is the conversion,
Bi is bromine index,
$S_{2-alkylbenzene}$ is selectivity for 2-alkylbenzene,
$S_{alkylbenzene}$ is selectivity for alkylbenzene;
$y_{i\ alkylbenzene}$ is the content by wt % of alkylbenzene having i carbon atoms,
$y_{i2-alkylbenzene}$ is the content by wt % of 2-alkylbenzene having i carbon atoms,
$y_{i\ heavy\ alkylbenzene}$ is the content by wt % of heavy alkyl benzene having i carbon atoms.

EXAMPLES

The present invention is further demonstrated with referring to the following Examples, but is not limited thereby.

Example 1

Figure 1:
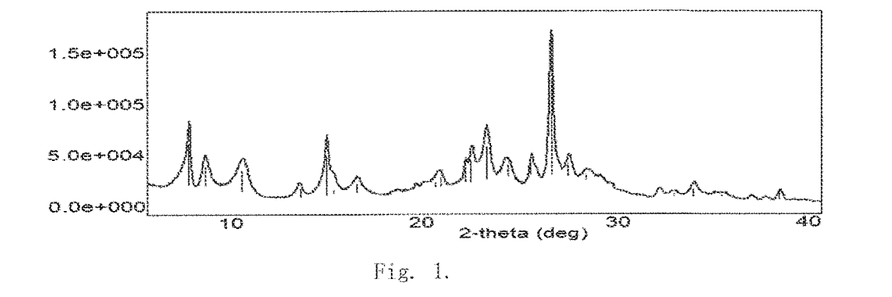
FIG. 1 is a X-ray diffraction pattern of the P-modified hydrogen-form MCM-22 type molecular sieve prepared according to Example 1.

Silica sol was used as silicon source, aluminum sulfate was used as aluminum source, piperidine was used as template agent, phosphoric acid was used as modifying heteroatom agent, and potassium hydroxide was used to adjust the pH. In all Examples and Comparative Examples of the present invention, the silica sol is provided by Yantai Thinking Fine Chemical Technology Co., Ltd., aluminum sulfate is provided by Zibo Guangzheng Aluminum Salt Chemical Co., Ltd., piperidine and the heteroatom agent are purchased from Nanjing Reagent Co., Ltd. The raw materials in molar ratio of $SiO_2:Al_2O_3:OH^-:P:TA:H_2O=1:0.03:0.2:0.01:0.3:25$ were charged into an autoclave and were stirred uniformly. The raw materials were subjected to a dynamic hydrothermal synthesis for 72 hours at a crystallization temperature of 160° C. and under self-generated pressure. The crystalized product, after filtration and washing, was dried at 120° C. for 6 hours. The temperature was programmably increased to 550° C. to remove the organic template agent. The resulting product was exchanged by using a 10% ammonium chloride aqueous solution at a liquid-to-solid mass ratio of 5:1 at a temperature of 80° C. for 5 hours, and the exchanging was conducted twice. The potassium content was measured to be less than 1000 ppm. After drying and roasting, P-modified hydrogen form MCM-22 type molecular sieve was obtained. XRD pattern was shown in FIG. 1. It can be confirmed from FIG. 1 that MCM-22 type molecular sieve was prepared.

A binder was added to the molecular sieve and the molecular sieve was extrusion shaped, dried and roasted to obtain alkylation solid acid catalyst AC-1. Characterization data are summarized in Table 1.

Example 2

Figure 2:
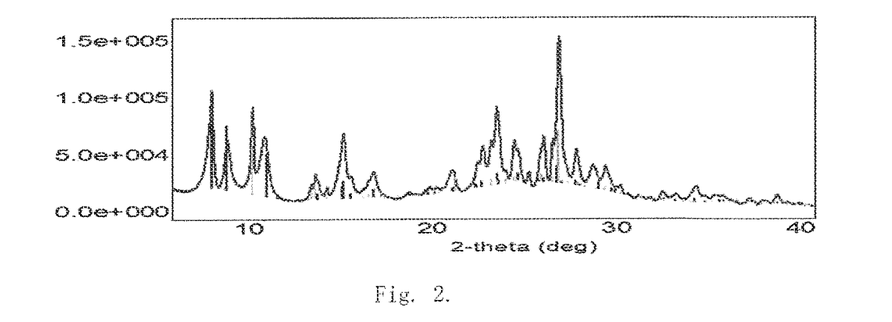
FIG. 2 is a X-ray diffraction pattern of the W-modified hydrogen-form MCM-22 type molecular sieve prepared according to Example 2.

Silica sol was used as silicon source, aluminum sulfate was used as aluminum source, piperidine was used as template agent, sodium tungstate was used as modifying heteroatom agent, and sodium hydroxide was used to adjust the pH. The raw materials in molar ratio of $SiO_2:Al_2O_3:OH^-:W:TA:H_2O=1:0.08:0.5:0.01:0.6:40$ were charged into an autoclave and were stirred uniformly. The raw materials were subjected to a dynamic hydrothermal synthesis for 96 hours at 180° C. and under self-generated pressure. The crystalized product, after filtration and washing, was dried at 120° C. for 6 hours. The temperature was programmably increased to 550° C. to remove the organic template agent. The resulting product was exchanged by using an aqueous solution of 20% ammonium chloride at a liquid-to-solid mass ratio of 6:1 at a temperature of 60° C. for 3 hours, and the exchanging was conducted twice. The sodium content was measured to be less than 1000 ppm. After drying and roasting, W-modified hydrogen form MCM-22 type molecular sieve was obtained. XRD pattern was shown in FIG. 2. It can be confirmed from FIG. 2 that MCM-22 type molecular sieve was prepared.

A binder was added to the molecular sieve and the molecular sieve was extrusion shaped, dried and roasted to obtain alkylation solid acid catalyst AC-2. Characterization data are summarized in Table 1.

Example 3

Figure 3:
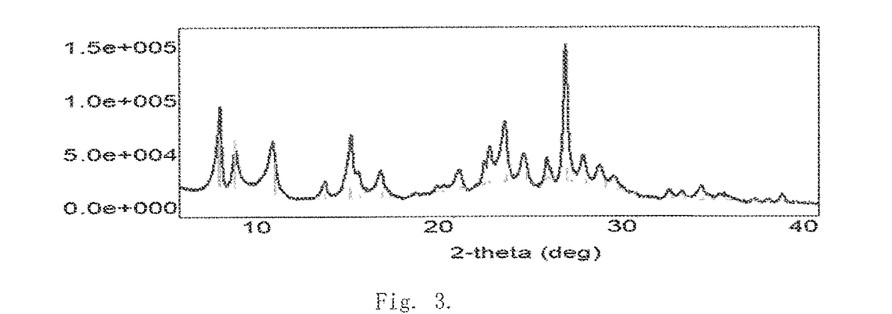
FIG. 3 is a X-ray diffraction pattern of the Mo-modified hydrogen-form MCM-22 type molecular sieve prepared according to Example 3.

Silica sol was used as silicon source, aluminum sulfate was used as aluminum source, piperidine was used as template agent, sodium molybdate was used as modifying heteroatom agent, and sodium hydroxide was used to adjust the pH. The raw materials in molar ratio of $SiO_2:Al_2O_3:OH^-:Mo:TA:H_2O=1:0.06:0.4:0.02:0.4:45$ were charged into an autoclave and were stirred uniformly. The raw materials were subjected to a dynamic hydrothermal synthesis for 120 hours at 150° C. and under self-generated pressure. The crystalized product, after filtration and washing, was dried at 120° C. for 6 hours. The temperature was programmably increased to 550° C. to remove the organic template agent. The resulting product was exchanged by using an aqueous solution of 10% ammonium nitrate at a liquid-to-solid mass ratio of 10:1 at a temperature of 90° C. for 3 hours, and the exchanging was conducted twice. The sodium content was measured to be less than 1000 ppm. After drying and roasting, Mo-modified hydrogen form MCM-22 type molecular sieve was obtained. XRD pattern was shown in FIG. 3. It can be confirmed from FIG. 3 that MCM-22 type molecular sieve was prepared.

A binder was added to the molecular sieve and the molecular sieve was extrusion shaped, dried and roasted to obtain alkylation solid acid catalyst AC-3. Characterization data are summarized in Table 1.

Comparative Example 1

Figure 4:
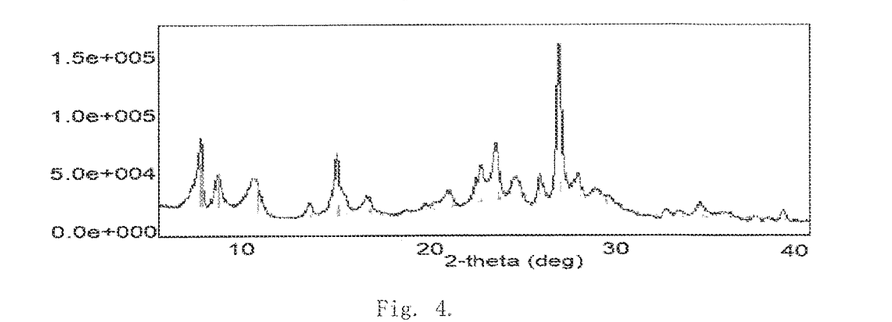
FIG. 4 is a X-ray diffraction pattern of the unmodified hydrogen-form MCM-22 type molecular sieve prepared according to Comparative Example 1.

Silica sol was used as silicon source, pseudo-boehmite was used as aluminum source, piperidine was used as template agent, and potassium hydroxide was used to adjust the pH. The raw materials in molar ratio of $SiO_2:Al_2O_3$:

OH⁻:TA:H₂O=1:0.03:0.2:0.3:25 were charged into an autoclave and were stirred uniformly. The raw materials were subjected to a dynamic hydrothermal synthesis for 72 hours at 160° C. and under self-generated pressure. The crystalized product, after filtration and washing, was dried at 120° C. for 6 hours. The temperature was programmably increased to 550° C. to remove the organic template agent. The resulting product was exchanged by using an aqueous solution of 10% ammonium chloride at a liquid-to-solid mass ratio of 5:1 at a temperature of 80° C. for 5 hours, and the exchanging was conducted twice. The potassium content was measured to be less than 1000 ppm. After drying and roasting, hydrogen form MCM-22 type molecular sieve without hetero-atom modification was obtained. XRD pattern was shown in FIG. 4. It can be confirmed from FIG. 4 that MCM-22 type molecular sieve was prepared.

A binder was added to the molecular sieve and the molecular sieve was extrusion shaped, dried and roasted to obtain alkylation solid acid catalyst CE-1. Characterization data are summarized in Table 1.

Comparative Example 2

Figure 5:
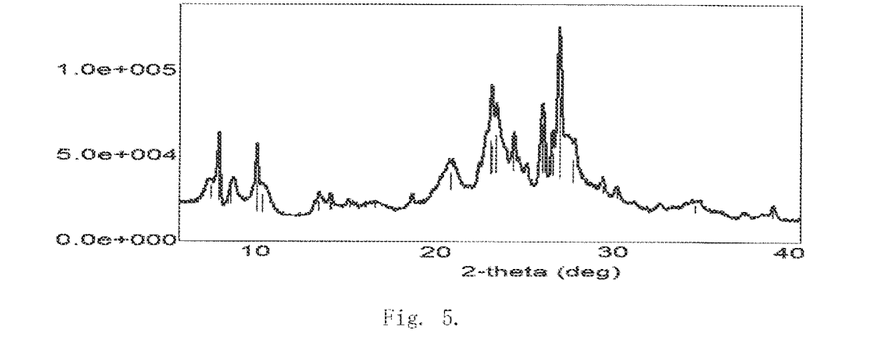
FIG. 5 is a X-ray diffraction pattern of the P-modified hydrogen-form MCM-22 type molecular sieve prepared according to Comparative Example 2, wherein the molar ratio of silicon atoms to phosphorus atoms does not fall within the scope of the present invention.

Silica sol was used as silicon source, aluminum sulfate was used as aluminum source, piperidine was used as template agent, phosphoric acid was used as modifying heteroatom agent, and potassium hydroxide was used to adjust the pH. The raw materials in molar ratio of $SiO_2$:$Al_2O_3$:OH⁻:P:TA:H₂O=1:0.03:0.2:0.04:0.3:25 were charged into an autoclave and were stirred uniformly. The raw materials were subjected to a dynamic hydrothermal synthesis for 72 hours at 160° C. and under self-generated pressure. The crystalized product, after filtration and washing, was dried at 120° C. for 6 hours. The temperature was programmably increased to 550° C. to remove the organic template agent. The resulting product was exchanged by using an aqueous solution of 10% ammonium chloride at a liquid-to-solid mass ratio of 5:1 at a temperature of 80° C. for 5 hours, and the exchanging was conducted twice. The potassium content was measured to be less than 1000 ppm. After drying and roasting, P-modified hydrogen form MCM-22 type molecular sieve was obtained. XRD pattern was shown in FIG. 5. It can be confirmed from FIG. 5 that MCM-22 type molecular sieve was prepared which has a lower crystallinity.

A binder was added to the molecular sieve and the molecular sieve was extrusion shaped, dried and roasted to obtain alkylation solid acid catalyst CE-2. Characterization data are summarized in Table 1.

Comparative Example 3

Figure 6:
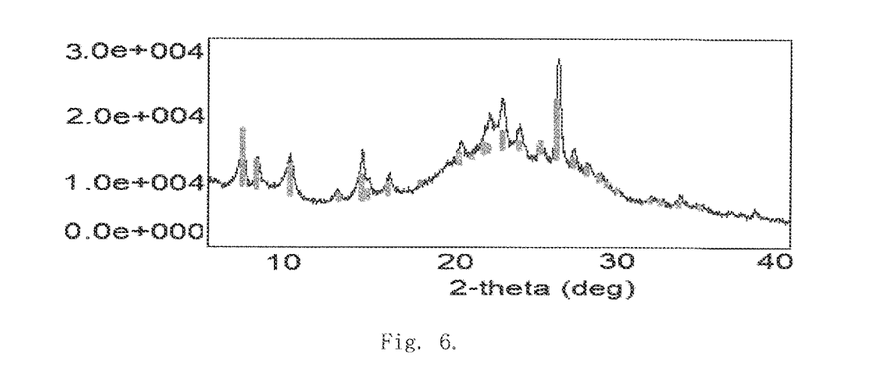
FIG. 6 is a X-ray diffraction pattern of the W-modified hydrogen-form MCM-22 type molecular sieve prepared according to Comparative Example 3, wherein the molar ratio of silicon atoms to tungsten atoms does not fall within the scope of the present invention.

Silica sol was used as silicon source, aluminum sulfate was used as aluminum source, piperidine was used as template agent, sodium tungstate was used as modifying heteroatom agent, and potassium hydroxide was used to adjust the pH. The raw materials in molar ratio of $SiO_2$:$Al_2O_3$:OH⁻:W:TA:H₂O=1:0.08:0.5:0.05:0.6:40 were charged into an autoclave and were stirred uniformly. The raw materials were subjected to a dynamic hydrothermal synthesis for 96 hours at 180° C. and under self-generated pressure. The crystalized product, after filtration and washing, was dried at 120° C. for 6 hours. The temperature was programmably increased to 550° C. to remove the organic template agent. The resulting product was exchanged by using an aqueous solution of 20% ammonium chloride at a liquid-to-solid mass ratio of 6:1 at a temperature of 60° C. for 3 hours, and the exchanging was conducted twice. The sodium content was measured to be less than 1000 ppm. After drying and roasting, W-modified hydrogen form MCM-22 type molecular sieve was obtained. XRD pattern was shown in FIG. 6. It can be confirmed from FIG. 6 that MCM-22 type molecular sieve was prepared which has a lower crystallinity.

A binder was added to the molecular sieve and the molecular sieve was extrusion shaped, dried and roasted to obtain alkylation solid acid catalyst CE-3. Characterization data are summarized in Table 1.

Comparative Example 4

Figure 7:
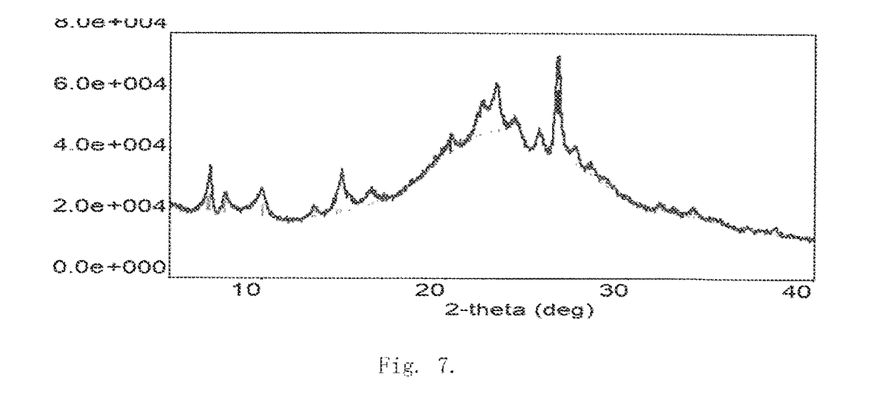
FIG. 7 is a X-ray diffraction pattern of the Mo-modified hydrogen-form MCM-22 type molecular sieve prepared according to Comparative Example 4, wherein the molar ratio of silicon atoms to molybdenum atoms does not fall within the scope of the present invention.

Silica sol was used as silicon source, aluminum sulfate was used as aluminum source, piperidine was used as template agent, sodium molybdate was used as modifying heteroatom agent, and sodium hydroxide was used to adjust the pH. The raw materials in molar ratio of $SiO_2$:$Al_2O_3$:OH⁻:Mo:TA:H₂O=1:0.06:0.4:0.06:0.4:45 were charged into an autoclave and were stirred uniformly. The raw materials were subjected to a dynamic hydrothermal synthesis for 120 hours at 150° C. and under self-generated pressure. The crystalized product, after filtration and washing, was dried at 120° C. for 6 hours. The temperature was programmably increased to 550° C. to remove the organic template agent. The resulting product was exchanged by using an aqueous solution of 10% ammonium nitrate at a liquid-to-solid mass ratio of 10:1 at a temperature of 90° C. for 3 hours, and the exchanging was conducted twice. The sodium content was measured to be less than 1000 ppm. After drying and roasting, Mo-modified hydrogen form MCM-22 type molecular sieve was obtained. XRD pattern was shown in FIG. 7. It can be confirmed from FIG. 7 that MCM-22 type molecular sieve was prepared which has a lower crystallinity.

A binder was added to the molecular sieve and the molecular sieve was extrusion shaped, dried and roasted to obtain alkylation solid acid catalyst CE-4. Characterization data are summarized in Table 1.

Example 4

The catalyst AC-1 was charged into a fixed bed reactor, and benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The reaction conditions were: temperature 160° C., pressure 2.0 MPa, and olefin liquid hourly space velocity 0.2 hr⁻¹; the reaction result is summarized in Table 2.

Example 5

The catalyst AC-2 was charged into a fixed bed reactor, and benzene and $C_{12}$ branched olefin were used as raw materials, wherein the olefin content in the branched olefin was 99%, and the molar ratio of benzene to olefin in the raw materials was 20. The reaction conditions were: temperature 180° C., pressure 3.0 MPa, and olefin liquid hourly space velocity 0.3 hr⁻¹; the reaction result is summarized in Table 2.

Example 6

The catalyst AC-3 was charged into a fixed bed reactor, and toluene and $C_{20}$-$C_{22}$ linear olefins were used as raw materials, wherein the α-linear olefin content in the linear olefins was 86%, and the molar ratio of benzene to olefin in the raw materials was 15. The reaction conditions were: temperature 200° C., pressure 4.0 MPa, and olefin liquid hourly space velocity 0.4 hr$^{-1}$; the reaction result is summarized in Table 2.

Example 7

The catalyst CE-1 was charged into a fixed bed reactor, and benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The reaction conditions were: temperature 160° C., pressure 2.0 MPa, and olefin liquid hourly space velocity 0.2 hr$^{-1}$; the reaction result is summarized in Table 2.

Example 8

The catalyst CE-2 was charged into a fixed bed reactor, and benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The reaction conditions were: temperature 160° C., pressure 2.0 MPa, and olefin liquid hourly space velocity 0.2 hr$^{-1}$; the reaction result is summarized in Table 2.

Example 9

The catalyst CE-3 was charged into a fixed bed reactor, and benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The reaction conditions were: temperature 160° C., pressure 2.0 MPa, and olefin liquid hourly space velocity 0.2 hr$^{-1}$; the reaction result is summarized in Table 2.

Example 10

The catalyst CE-4 was charged into a fixed bed reactor, and benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The reaction conditions were: temperature 160° C., pressure 2.0 MPa, and olefin liquid hourly space velocity 0.2 hr$^{-1}$; the reaction result is summarized in Table 2.

Example 11

On the basis of Example 4, the catalyst was regenerated by burning the coke after deactivation, and the coke burning conditions were as follows:

The oxygen content in the regeneration gas was 5 wt %, with the rest being nitrogen, and the volumetric space velocity of the regeneration gas was 500 hr$^{-1}$. The coke burning temperature was arranged into four temperature stages, i.e. 200° C., 350° C., 450° C. and 520° C., wherein the temperature was increased from room temperature to 200° C. at a rate of 35° C./h, and the temperature was maintained at 200° C. for 7 hours; the temperature was increased from 200° C. to 350° C. at a rate of 25° C./h, and the temperature was maintained at 350° C. for 7 hours; the temperature was increased from 350° C. to 450° C. at a rate of 20° C./h, and the temperature was maintained at 450° C. for 7 hours; and the temperature was increased from 450° C. to 520° C. at a rate of 10° C./h, and the temperature was maintained at 520° C. for 7 hours. After the completion of coke-burning, the catalyst cooled naturally. The catalyst characterization data are summarized in Table 1.

Benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The raw materials were fed into a fixed bed reactor loaded with regenerated catalyst AC-1, wherein the reaction conditions were: temperature 160° C., pressure 2.0 MPa, and olefin liquid hourly space velocity 0.2 Hr$^{-1}$. The reaction results are summarized in Table 2.

Example 12

On the basis of Example 5, the catalyst was regenerated by burning the coke after deactivation, and the coke burning conditions were as follows:

The oxygen content in the regeneration gas was 10 wt %, with the rest being nitrogen, and the volumetric space velocity of the regeneration gas was 500 hr$^{-1}$. The coke burning temperature was arranged into four temperature stages, i.e. 200° C., 350° C., 450° C. and 520° C., wherein the temperature was increased from room temperature to 200° C. at a rate of 30° C./h, and the temperature was maintained at 200° C. for 8 hours; the temperature was increased from 200° C. to 350° C. at a rate of 20° C./h, and the temperature was maintained at 350° C. for 8 hours; the temperature was increased from 350° C. to 450° C. at a rate of 25° C./h, and the temperature was maintained at 450° C. for 8 hours; and the temperature was increased from 450° C. to 520° C. at a rate of 15° C./h, and the temperature was maintained at 520° C. for 6 hours. After the completion of coke-burning, the catalyst cooled naturally. The catalyst characterization data are summarized in Table 1.

Benzene and $C_{12}$ branched olefin were used as raw materials, wherein the olefin content in the branched olefin was 99%, and the molar ratio of benzene to olefin in the raw materials was 20. The raw materials were fed into a fixed bed reactor loaded with regenerated catalyst AC-2, wherein the reaction conditions were: temperature 180° C., pressure 3.0 MPa, and olefin liquid hourly space velocity 0.3 Hr$^{-1}$. The reaction results are summarized in Table 2.

Example 13

On the basis of Example 6, the catalyst was regenerated by burning the coke after deactivation, and the coke burning conditions were as follows:

The oxygen content in the regeneration gas was 8 wt %, with the rest being nitrogen, and the volumetric space velocity of the regeneration gas was 500 hr$^{-1}$. The coke burning temperature was arranged into four temperature stages, i.e. 200° C., 350° C., 450° C. and 520° C., wherein the temperature was increased from room temperature to 200° C. at a rate of 30° C./h, and the temperature was maintained at 200° C. for 9 hours; the temperature was increased from 200° C. to 350° C. at a rate of 20° C./h, and the temperature was maintained at 350° C. for 9 hours; the temperature was increased from 350° C. to 450° C. at a rate of 20° C./h, and the temperature was maintained at 450° C. for 9 hours; and the temperature was increased from 450° C. to 520° C. at a rate of 15° C./h, and the temperature was maintained at 520° C. for 5 hours. After the completion of coke-burning, the catalyst cooled naturally. The catalyst characterization data are summarized in Table 1.

Toluene and $C_{20}$-$C_{22}$ olefins were used as raw materials, wherein the α-linear olefin content in the olefins was 86%, and the molar ratio of benzene to olefin in the raw materials was 15:1. The raw materials were fed into a fixed bed reactor loaded with regenerated catalyst AC-3, wherein the reaction conditions were: temperature 200° C., pressure 4.0 MPa, and olefin liquid hourly space velocity 0.4 $Hr^{-1}$. The reaction results are summarized in Table 2.

Example 14

On the basis of Example 7, the catalyst was regenerated by burning the coke after deactivation, and the coke burning conditions were as follows:

The oxygen content in the regeneration gas was 5 wt %, with the rest being nitrogen, and the volumetric space velocity of the regeneration gas was 500 $hr^{-1}$. The coke burning temperature was arranged into four temperature stages, i.e. 200° C., 350° C., 450° C. and 520° C., wherein the temperature was increased from room temperature to 200° C. at a rate of 35° C./h, and the temperature was maintained at 200° C. for 7 hours; the temperature was increased from 200° C. to 350° C. at a rate of 25° C./h, and the temperature was maintained at 350° C. for 7 hours; the temperature was increased from 350° C. to 450° C. at a rate of 20° C./h, and the temperature was maintained at 450° C. for 7 hours; and the temperature was increased from 450° C. to 520° C. at a rate of 10° C./h, and the temperature was maintained at 520° C. for 7 hours. After the completion of coke-burning, the catalyst cooled naturally. The catalyst characterization data are summarized in Table 1.

Benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The raw materials were fed into a fixed bed reactor loaded with regenerated catalyst CE-1, wherein the reaction conditions were: temperature 160° C., pressure 2.0 MPa, and olefin liquid hourly space velocity 0.2 $Hr^{-1}$. The reaction results are summarized in Table 2.

Regeneration Comparative Example 1

On the basis of Example 11, the catalyst was regenerated after deactivation by flushing with benzene. The regeneration conditions were as follows: temperature 280° C., pressure 4 MPa, and space velocity 2.0 $h^{-1}$. After 24 hours, the flushing was stopped, the temperature was lowered and the regeneration ended. The regenerated catalyst was named as benzene-flushing regenerated catalyst AC-1, and the characterization data are summarized in Table 1.

Benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The raw materials were fed into a fixed bed reactor loaded with benzene-flushing regenerated catalyst AC-1, wherein the reaction conditions were: temperature 160° C., pressure 2.0 MPa, and olefin liquid hourly space velocity 0.2 $Hr^{-1}$. The reaction results are summarized in Table 2.

Example 15

On the basis of Regeneration Comparative Example 1, the catalyst was regenerated by burning the coke after deactivation, and the coke burning conditions were as follows: The oxygen content in the regeneration gas was 12%, with the rest being nitrogen, and the volumetric space velocity of the regeneration gas was 500 $hr^{-1}$. The coke burning temperature was arranged into four temperature stages, i.e. 200° C., 350° C., 450° C. and 520° C., wherein the temperature was increased from room temperature to 200° C. at a rate of 30° C./h, and the temperature was maintained at 200° C. for 5 hours; the temperature was increased from 200° C. to 350° C. at a rate of 20° C./h, and the temperature was maintained at 350° C. for 8 hours; the temperature was increased from 350° C. to 450° C. at a rate of 25° C./h, and the temperature was maintained at 450° C. for 10 hours; and the temperature was increased from 450° C. to 520° C. at a rate of 5° C./h, and the temperature was maintained at 520° C. for 5 hours. After the completion of coke-burning, the catalyst cooled naturally. The catalyst was named as third regeneration catalyst AC-1, and the characterization data are summarized in Table 1.

Benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The raw materials were fed into a fixed bed reactor loaded with third regeneration catalyst AC-1, wherein the reaction conditions were: temperature 160° C., pressure 2.0 MPa, and olefin liquid hourly space velocity 0.2 $Hr^{-1}$. The reaction results are summarized in Table 2.

Regeneration Comparative Example 2

On the basis of Example 15, the catalyst was regenerated by burning the coke after deactivation, and the coke burning conditions were as follows:

The oxygen content in the regeneration gas was 15%, with the rest being nitrogen, and the volumetric space velocity of the regeneration gas was 500 $hr^{-1}$. The coke burning temperature dud not have any stages, and the temperature was increased directly from room temperature to 520° C. at a rate of 5° C./h, and the temperature was maintained at 520° C. for 10 hours. After the completion of coke-burning, the catalyst cooled naturally. The catalyst was named as direct-temperature-increasing regeneration catalyst AC-1, and the characterization data are summarized in Table 1.

Benzene and a mixture of $C_{10}$-$C_{13}$ linear alkanes and olefins were used as raw materials, wherein the linear olefin content in the linear alkanes and olefins mixture was 10%, and the molar ratio of benzene to olefin in the raw materials was 10. The raw materials were fed into a fixed bed reactor loaded with direct-temperature-increasing regeneration catalyst AC-1, wherein the reaction conditions were: temperature 160° C., pressure 2.0 MPa, and olefin liquid hourly space velocity 0.2 $Hr^{-1}$. The reaction results are summarized in Table 2.

TABLE 1

Physical Property Characterizations of Catalysts

| Catalyst | Specific surface area ($m^2$/g) | Pore volume (ml/g) | L acid amount ($10^{20}$ sites/ g · cat) | B acid amount ($10^{20}$ sites/ g · cat) |
|---|---|---|---|---|
| AC-1 | 419 | 0.389 | 2.43 | 2.94 |
| AC-2 | 411 | 0.392 | 2.51 | 2.82 |
| AC-3 | 428 | 0.403 | 2.77 | 2.86 |
| CE-1 | 408 | 0.386 | 2.62 | 2.89 |

TABLE 1-continued

Physical Property Characterizations of Catalysts

| Catalyst | Specific surface area (m²/g) | Pore volume (ml/g) | L acid amount ($10^{20}$ sites/ g · cat) | B acid amount ($10^{20}$ sites/ g · cat) |
|---|---|---|---|---|
| CE-2 | 356 | 0.326 | 2.13 | 2.24 |
| CE-3 | 283 | 0.274 | 1.35 | 1.54 |
| CE-4 | 301 | 0.288 | 1.71 | 1.83 |
| regenerated AC-1 | 415 | 0.383 | 2.45 | 2.91 |
| regenerated AC-2 | 413 | 0.391 | 2.48 | 2.78 |
| regenerated AC-3 | 421 | 0.398 | 2.63 | 2.82 |
| regenerated CE-1 | 403 | 0.384 | 2.57 | 2.81 |
| benzene-flushing regenerated AC-1 | 306 | 0.265 | 1.42 | 1.56 |
| third regenerated AC-1 | 412 | 0.384 | 2.43 | 2.90 |
| direct-temperature-increasing regenerated AC-1 | 381 | 0.339 | 2.26 | 2.47 |

The catalysts prepared according to the methods of the present invention have high crystallinity, high specific surface area, high pore volume and high acid amounts, especially high total acid amount, compared to the catalysts prepared in Comparative Examples 2-4.

As can be seen from Table 1, the catalysts regenerated according to the regeneration methods of the present invention do not exhibit significant reductions in specific surface area, pore volume, and acid amounts, even in the case of multiple regenerations. In contrast, the catalyst regenerated by benzene flushing according to prior art cannot flush away deposited carbon completely, and exhibits a significant reduction in specific surface area, pore volume and acid amounts. The catalyst regenerated by direct-temperature-increasing tends to sinter the catalyst, resulting in the reduction of specific surface area, pore volume and acid amounts.

catalysts regenerated according to the regeneration methods of the present invention exhibit similar high olefin conversion and alkylbenzene selectivity, even after multiple regenerations. Such olefin conversions are much higher than those prepared according to Comparative Examples 2-4. The catalysts regenerated according to the regeneration methods according to the present invention exhibit significantly higher olefin conversions than the catalyst regenerated using benzene flushing.

As can be seen from the results in Table 2, the catalysts prepared as in Examples 1-3 and used in accordance with the present invention exhibit higher 2-position alkylbenzene selectivity than catalysts prepared in accordance with Comparative Examples 2-4. The catalysts regenerated according to the regeneration methods according to the present invention exhibit significantly higher 2-position alkylbenzene selectivity than the catalyst regenerated using benzene flushing.

As can be seen from the results in Table 2, the catalysts prepared as in Examples 1-3 and used in accordance with the present invention exhibit higher stability than the catalyst prepared in accordance with Comparative Example 1, particularly as shown by the longer continuous running time. The catalysts prepared in accordance with Comparative Examples 2-4 do not have the ability for a long time stable running. The catalyst regenerated by using the regeneration method according to the present invention exhibits a higher stability than the catalysts regenerated by using benzene flushing and direct-temperature-increasing, particularly as shown by the longer continuous running time.

The invention claimed is:

1. A method for producing long-chain alkylbenzene by reacting an aromatic hydrocarbon and a long-chain olefin, characterized in that the reaction is carried out in the presence of a solid acid catalyst, the aromatic hydrocarbon is selected from the group consisting of benzene, toluene and xylene, the long-chain olefin is selected from the group

TABLE 2

Reaction Results of Catalysts

| Example | Catalyst | Olefin Conversion (%) | Alkylbenzene Selectivity (%) | 2-position alkylbenzene Selectivity (%) | Continuous Running Time (hours) |
|---|---|---|---|---|---|
| 4 | AC-1 | 99.9 | 99.4 | 47.3 | 2020 |
| 5 | AC-2 | 99.2 | 99.3 | — | 2015 |
| 6 | AC-3 | 99.8 | 99.2 | 43.8 | 2008 |
| 7 | CE-1 | 99.8 | 99.5 | 40.6 | 344 |
| 8 | CE-2 | 83.2 | 98.7 | 42.6 | — |
| 9 | CE-3 | 24.9 | 99.1 | 41.7 | — |
| 10 | CE-4 | 47.4 | 98.8 | 42.8 | — |
| 11 | regenerated AC-1 | 99.8 | 99.3 | 47.8 | 2012 |
| 12 | regenerated AC-2 | 99.2 | 99.7 | — | 2010 |
| 13 | regenerated AC-3 | 99.7 | 99.4 | 44.5 | 2005 |
| 14 | Regenerated CE-1 | 99.6 | 99.6 | 40.2 | 338 |
| Regeneration Comparative Example 1 | benzene-flushing regenerated AC-1 | 52.3 | 99.6 | 43.9 | — |
| 15 | third regenerated AC-1 | 99.8 | 99.4 | 47.1 | 2017 |
| Regeneration Comparative Example 2 | direct-temperature-increasing regenerated AC-1 | 99.1 | 98.9 | 46.4 | 839 |

As can be seen from the results in Table 2, the catalysts prepared as in Examples 1-3 and used in accordance with the present invention exhibit high olefin conversion and alkylbenzene selectivity which are both higher than 99%. The consisting of $C_8$-$C_{26}$ alkenes, the solid acid catalyst is a HMCM-22 molecular sieve solid acid catalyst modified with heteroatom(s), the heteroatom(s) is/are selected from the group consisting of boron, gallium, indium, chromium, molybdenum, tungsten, manganese and phosphorus, and the molar ratio of silicon atoms to heteroatoms in the solid acid catalyst is in a range of 1:0.01-0.03, wherein the solid acid catalyst is prepared by a method comprising the following steps:
- a) formulating silicon source, aluminum source, heteroatom modifier, pH regulator, organic template agent and water in a certain proportion so as to form a synthetic colloid, and subjecting the synthetic colloid to a hydrothermal crystallization to form a crystallized product, wherein the molar ratio of the silicon source, aluminum source, heteroatom modifier, pH regulator, organic template agent and water $SiO_2:Al_2O_3:OH^-:M:TA:H_2O$ is 1:0.01-0.1:0.1-0.5:0.01-0.03:0.3-0.6:20-50, where $SiO_2$ represents the silicon source calculated by $SiO_2$, $Al_2O_3$ represents the aluminum source calculated by $Al_2O_3$, $OH^-$ represents the pH regulator calculated by $OH^-$, TA represents the organic template agent, and M represents the heteroatoms in the heteroatom modifier;
- b) filtering, washing and drying the crystallized product and calcining at 500-600° C. to remove the template agent so as to obtain Na or K form MCM-22 molecular sieve.
- c) exchanging the molecular sieve into HMCM-22 molecular sieve by using ammonium chloride and/or ammonium nitrate as exchanger, wherein the Na or K content of the HMCM-22 molecular sieve after exchanging is less than 1000 ppm, and drying and roasting the HMCM-22 molecular sieve;
- d) adding a binder into the HMCM-22 molecular sieve, shaping, drying, and calcining at 500-600° C. so as to obtain the HMCM-22 molecular sieve solid acid catalyst.

2. The method of claim 1, characterized in that the reaction uses a fixed bed reactor so as to carry out a continuous liquid phase reaction, wherein the reaction temperature is from 100 to 300° C., the reaction pressure is from 1 to 5 MPa, and the liquid hourly space velocity of the reaction is from 0.1 to 5 $Hr^{-1}$.

3. The method of claim 1, characterized in that the molar ratio of aromatic hydrocarbon to long-chain olefin is from 1 to 30.

4. The method of claim 1, characterized in that the silicon source is selected from the group consisting of silica gel, silica sol, water glass, silicic acid, sodium silicate, methyl orthosilicate, and ethyl orthosilicate.

5. The method of claim 1, characterized in that the aluminum source is selected from the group consisting of sodium metaaluminate, aluminum sulfate, aluminum nitrate, and pseudo-boehmite.

6. The method of claim 1, characterized in that the organic template agent is selected from the group consisting of hexamethyleneimine, caprolactam and piperidine.

7. The method of claim 1, characterized in that the pH regulator is selected from the group consisting of potassium hydroxide and sodium hydroxide.

8. The method of claim 1, characterized in that the heteroatom modifier is selected from the group consisting of phosphoric acid, sodium tungstate and gallium nitrate.

9. The method of claim 1, characterized in that the molar ratio of the silicon source, aluminum source, heteroatom modifier, pH regulator, organic template agent and water $SiO_2:Al_2O_3:OH^-:M:TA:H_2O$ is 1:0.05-0.08:0.2-0.3:0.01-0.02:0.4-0.5:30-40, where $SiO_2$ represents the silicon source calculated by $SiO_2$, $Al_2O_3$ represents the aluminum source calculated by $Al_2O_3$, $OH^-$ represents the pH regulator calculated by $OH^-$, TA represents the organic template agent, and M represents the heteroatoms in the heteroatom modifier.

10. The method of claim 1, characterized in that, after the activity of the solid acid catalyst decreases, the solid acid catalyst is in-situ coke-burning regenerated by using an oxygen-containing inert gas.

11. The method of claim 10, characterized in that the solid acid catalyst is in-situ coke-burning regenerated by using a regeneration gas comprising 1-20 wt % of oxygen and 80-99 wt % of nitrogen, and the volumetric space velocity of the regeneration gas is 100-1000 $hr^{-1}$.

12. The method of claim 10, characterized in that the solid acid catalyst is in-situ coke-burning regenerated by using a regeneration gas comprising 2-15 wt % of oxygen and 85-98 wt % of nitrogen, and the volumetric space velocity of the regeneration gas is 300-500 $hr^{-1}$.

13. The method of claim 10, characterized in that during the coke-burning regeneration process, the temperature ramp rate for coke-burning is controlled by arranging five temperature stages including room temperature, 200° C., 350° C., 450° C. and 520° C., wherein the temperature ramp rate from room temperature to 200° C. is controlled at 10-40° C./h, and the temperature is maintained at 200° C. for 5-12 h; the temperature ramp rate from 200° C. to 350° C. is controlled at 15-25° C./h, and the temperature is maintained at 350° C. for 5-12 h; the temperature ramp rate from 350° C. to 450° C. is controlled at 10-30° C./h, and the temperature is maintained at 450° C. for 5-12 h; the temperature ramp rate from 450° C. to 520° C. is controlled at 5-15° C./h, and the temperature is maintained at 520° C. for 5-10 h.

14. The method of claim 10, characterized in that during coke-burning regeneration process, the temperature ramp rate for coke-burning is controlled by arranging five temperature stages including room temperature, 200° C., 350° C., 450° C. and 520° C., wherein the temperature ramp rate from room temperature to 200° C. is controlled at 20-30° C./h, and the temperature is maintained at 200° C. for 6-10 h; the temperature ramp rate from 200° C. to 350° C. is controlled at 18-22° C./h, and the temperature is maintained at 350° C. for 6-10 h; the temperature ramp rate from 350° C. to 450° C. is controlled at 15-25° C./h, and the temperature is maintained at 450° C. for 6-10 h; the temperature ramp rate from 450° C. to 520° C. is controlled at 8-12° C/h, and the temperature is maintained at 520° C. for 6-8 h.

* * * * *